United States Patent
Nourbakhsh et al.

(10) Patent No.: US 10,054,534 B1
(45) Date of Patent: Aug. 21, 2018

(54) GROUP CALIBRATION OF ENVIRONMENTAL SENSORS

(71) Applicant: Airviz Inc., Pittsburgh, PA (US)

(72) Inventors: Illah Nourbakhsh, Pittsburgh, PA (US); Joshua Schapiro, Pittsburgh, PA (US); Michael D. Taylor, Pittsburgh, PA (US)

(73) Assignee: Airviz Inc., Pittsburgh, PA (US)

( * ) Notice: Subject to any disclaimer, the term of this patent is extended or adjusted under 35 U.S.C. 154(b) by 105 days.

(21) Appl. No.: 15/156,954

(22) Filed: May 17, 2016

Related U.S. Application Data

(60) Provisional application No. 62/189,978, filed on Jul. 8, 2015.

(51) Int. Cl.
| | | |
|---|---|---|
| G01N 33/00 | (2006.01) | |
| G01D 18/00 | (2006.01) | |
| G01K 15/00 | (2006.01) | |
| G02B 6/00 | (2006.01) | |
| G01N 15/14 | (2006.01) | |
| G01N 15/06 | (2006.01) | |
| G01N 15/10 | (2006.01) | |

(52) U.S. Cl.
CPC ......... *G01N 15/1429* (2013.01); *G01N 15/06* (2013.01); *G01N 2015/0693* (2013.01); *G01N 2015/1068* (2013.01)

(58) Field of Classification Search
None
See application file for complete search history.

(56) References Cited

U.S. PATENT DOCUMENTS

| | | | | |
|---|---|---|---|---|
| 3,933,433 A | * | 1/1976 | Hooker | G01N 27/122 436/134 |
| 4,185,491 A | * | 1/1980 | Owen | G01N 27/124 73/31.06 |
| 4,279,142 A | * | 7/1981 | McIntyre | G01N 33/0006 73/1.06 |
| 4,364,234 A | * | 12/1982 | Reed | F25B 21/02 165/265 |

(Continued)

FOREIGN PATENT DOCUMENTS

| | | |
|---|---|---|
| WO | WO 2010/046711 A2 | 4/2010 |
| WO | WO 2014/005714 A1 | 1/2014 |
| WO | WO 2016/054004 A1 | 4/2016 |

*Primary Examiner* — Shawn Decenzo
*Assistant Examiner* — Jarreas C Underwood
(74) *Attorney, Agent, or Firm* — K&L Gates LLP

(57) ABSTRACT

Systems and methods batch calibrate environmental sensors. Candidate environmental sensors and a high-performance reference sensor are located in an enclosure with a particle excitation system that controls the particle concentration in the enclosure. The calibration process includes multiple phases with different particle concentrations, and the candidate and reference sensors continuously report their particle counts to a calibration server during these phases. Based on the collected data, the calibration server: (i) identifies for removal candidate sensors with outlying behavior through statistical analysis; and (ii) computes calibration values for the particle count estimation algorithms for the remaining candidate sensors that are optimized to minimize the error relative to the reference sensor(s).

17 Claims, 3 Drawing Sheets

(56) References Cited

U.S. PATENT DOCUMENTS

| | | | | |
|---|---|---|---|---|
| 4,384,925 | A * | 5/1983 | Stetter | G01N 33/0006 204/401 |
| 4,847,493 | A * | 7/1989 | Sodal | H01J 49/26 250/252.1 |
| 5,239,492 | A * | 8/1993 | Hartwig | G01N 33/0006 702/27 |
| 5,317,156 | A * | 5/1994 | Cooper | G01N 21/39 250/339.13 |
| 5,367,577 | A * | 11/1994 | Gotaas | G07D 7/12 382/135 |
| 6,171,366 | B1 * | 1/2001 | Vicard | B01D 46/0075 55/283 |
| 6,918,281 | B2 * | 7/2005 | Sussman | G01N 33/0006 73/1.03 |
| 7,201,033 | B2 * | 4/2007 | Wible | G01F 1/6965 73/1.16 |
| 7,401,493 | B2 * | 7/2008 | Forrest | G01N 33/0006 73/1.06 |
| 8,101,905 | B2 * | 1/2012 | Rogers | G01J 5/0022 250/252.1 |
| 8,220,308 | B2 * | 7/2012 | Bellis | G01N 33/0006 73/1.06 |
| 8,222,606 | B1 * | 7/2012 | Wong | G01N 21/274 250/252.1 |
| 8,993,956 | B2 * | 3/2015 | Engelhardt | G07D 7/12 250/252.1 |
| 9,057,636 | B2 * | 6/2015 | Nagai | G01F 25/0053 |
| 9,316,627 | B2 * | 4/2016 | Niiranen | G01N 33/0006 |
| 9,395,334 | B2 * | 7/2016 | Takasu | G01N 5/02 |
| 9,664,607 | B2 * | 5/2017 | Park | G01N 33/0036 |
| 2008/0225910 | A1 | 9/2008 | Lerner et al. | |
| 2009/0082987 | A1 | 3/2009 | Collins | |
| 2011/0031386 | A1 | 2/2011 | Pradel | |
| 2011/0072879 | A1 | 3/2011 | Bellis et al. | |
| 2012/0330596 | A1 * | 12/2012 | Kouznetsov | G01N 33/0006 702/104 |
| 2013/0325252 | A1 | 12/2013 | Schommer et al. | |
| 2014/0083159 | A1 | 3/2014 | Nagai | |
| 2014/0092933 | A1 | 4/2014 | Coursey et al. | |
| 2014/0180048 | A1 * | 6/2014 | Keith | A61B 5/1495 600/347 |
| 2014/0273042 | A1 | 9/2014 | Saint | |

* cited by examiner

US 10,054,534 B1

GROUP CALIBRATION OF ENVIRONMENTAL SENSORS

PRIORITY CLAIM

The present application claims priority to U.S. provisional patent application Ser. No. 62/189,978, filed Jul. 8, 2015, titled "Group Calibration of Air Quality Monitors," which is incorporated herein by reference in its entirety.

BACKGROUND

Significant bodies of research indicate that cumulative, personal exposure to fine particulates (i.e. $PM_{2.5}$) is strongly correlated with pulmonary disease and cardiovascular disease. In addition, statistically significant correlations have now been discovered between exposure to $PM_{2.5}$ by pregnant women and the onset of autism and attention deficit hyperactivity disorder in children. The residential home represents a large portion of a person's overall exposure profile to $PM_{2.5}$, and therefore direct measurement and reporting of home air pollution can provide valuable insight into mitigation of overall fine particular exposure in order to maximize long-term and short-term health. Existing low-cost devices suitable for retail sales suffer from lack of linearity and lack of value agreement, chiefly because particulate measurement sensitivity is greatly affected by individual electronics and optics components used in core particulate sensing devices.

In order to enable the sale of low-cost particle-counting air pollution or quality monitors, one must be able to calibrate the sensitivity and signal functions of each fully built air quality monitor individually. However, individual calibration is expensive in time and labor terms, thereby conflicting with the goal of keeping total production cost low so that the retail price may also be low.

SUMMARY

In one general aspect, the present invention is directed to systems and methods for batch (or group) calibration of environmental sensors, such as air quality monitors. The candidate sensors and a high-performance reference sensor are located in an enclosure (e.g., a calibration chamber) with a particle excitation system (preferably PM2.5 particles) that controls the particle concentration in the enclosure. The calibration process can include multiple phases with different particle concentrations in each phase, and the candidate and reference sensors continuously report their environmental readings (e.g., particle concentration readings) to a calibration server during these phases. Based on the collected data, the calibration server: (i) identifies for removal candidate sensors with outlying behavior through statistical analysis; and (ii) computes calibration values for the particle count estimation algorithms for the remaining candidate sensors that are optimized to minimize the error relative to the reference sensor(s).

This calibration process provides many advantages relative to existing environmental sensor calibration techniques. First, it lowers the calibration cost per sensor since they are calibrated in batch, which helps maintain a low overall cost for the sensor, making them more affordable to the general public. Second, sensors with outlying behavior can be efficiently and accurately identified and removed so that they are not placed in use. Third, the calibration values can be archived for quality control and diagnostic purposes. These and other benefits of the present invention will be apparent from the description that follows.

FIGURES

Various embodiments of the present invention are described herein by way of example in connection with the following figures, wherein.

DESCRIPTION

In one general aspect, the present invention is directed to systems and methods for calibrating a number of candidate environmental sensors in a group or batch. Before describing the group calibration process, details about an exemplary candidate environmental sensor M are first provided.

Figure 1:
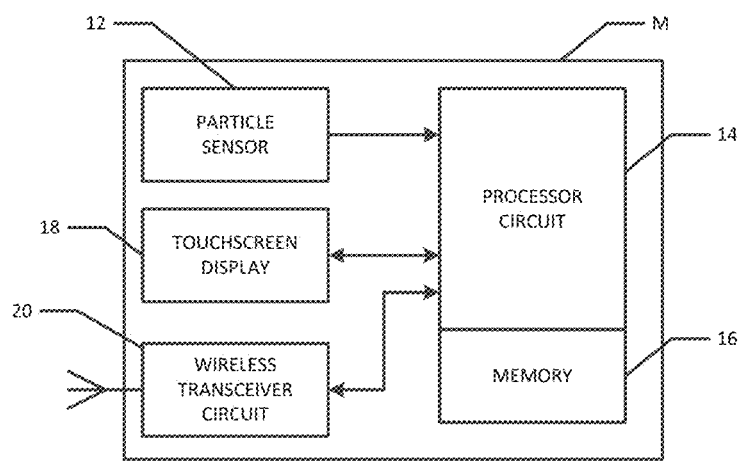
FIG. 1 is block diagram of an environmental sensor according to various embodiments of the present invention.

FIG. 1 is a block diagram of a candidate environmental sensor M according to various embodiments of the present invention. The illustrated environmental sensor M comprises an optical particle sensor 12, a programmable processor circuit (e.g., a microprocessor) 14 with associated memory 16 (e.g., on-board memory), a touch-screen display 18, and a wireless transceiver circuit 20 (e.g., a Wi-Fi module, chip or chipset). The particle sensor 12 subjects incoming ambient air around the sensor M to infrared LED illumination and measures reflections of infrared light by detecting short-term, perpendicular reflections using a photodetector chip in order to detect and count particles in the air around the sensor. The optical particle sensor 12 can be designed to detect and count particles that are 10 microns or less in diameters, and preferably 0.3 to 10 microns. Fine airborne particles smaller than 2.5 microns, often denoted as $PM_{2.5}$, can pose serious health risks. Thus, the particle sensor 12 preferably detects $PM_{2.5}$ particles. The sensor M is preferably for indoor use, such as in a user's home. That way, with the sensor M the user can continuously monitor the air quality in their home.

The particle sensor 12 may be, for example, a DSM501A dust sensor. The sensor can include a fan forcing inflow of the sampling air, and measures the dispersion of reflected lights (from an illuminating LED) by particles in an optical chamber of the particle sensor 12. This measurement is converted to a pulse width modulated (PWM) output signal. In particular, the particle sensor 12 can include a digital output connected to the microprocessor 14, where the digital pin voltage is pulled low when particles are detected in the sensor's optical chamber, with the duty cycle being approximately proportional to the number of detected particles.

The microprocessor 14, by executing code stored in the memory 16, implements an air quality estimation algorithm to compute an air quality measure (e.g., an environmental reading), records raw particle sensor output values, and uses these values to compute and store estimated particle concentration values or readings for the sensor's ambient air in memory 16. The computed particle concentration values can comprise volume-based concentration values (e.g., particles per liter) or mass-based concentration values (mg or µg per cubic cm). Additional resident firmware code in the memory 16 and executed by the processor 14 serves to control the pixels of the touch-screen display 18, which preferably is a color TFT touchscreen, in order to render interactive screens, detect screen touch events, and govern transitions between separate interactive screen modes, including real-time and historical review modes.

While the duration of the low pulses from the particle sensor 12 (indicating detected particles) rarely exceeds 100 ms, the duration between pulses can last from under one second to more than one minute. Because single-cycle readings are typically too noisy to be used directly, in various embodiments the processor's algorithm samples the sensor output, such as 10,000 times per second. The number of low samples each second can be used by the processor's estimation algorithm to determine the particle count. In one embodiment, an asymmetric filtering function can be used. In one embodiment, the processor 14 can use the following piecewise function to continuously update the cumulative particle count estimate $est_t$ at time t, where $raw_t$ is the raw sensor value at time t:

$$est_{t=1} = \begin{cases} \dfrac{A * raw_t - est_t}{B} + est_t, & \text{where } raw_t > 0 \\ (1-D) * est_t, & \text{where } raw_t = 0 \end{cases} \quad \text{Equation (1)}$$

A, B, and D are constants (e.g., calibration values) that can be determined through the calibration process that is described herein. As Equation 1 shows, if the raw value is non-zero, the current particle count estimate is incremented or decremented at a rate proportional to the difference between the estimate and the raw value scaled by a constant. If the raw value is zero, the estimate exponentially decays toward zero, preferably at a lower rate. The resulting behavior is that the particle count estimate quickly responds to non-zero raw values, but decays toward zero slowly due to the potential for long pauses between pulses. The processor 14 can also be programmed to convert the particle count to an estimated particle weight (e.g., micrograms per cubic meter).

The wireless transceiver subsystem 20 is commanded by the microprocessor 14 to establish, in various embodiments, a Wi-Fi (IEEE 802.11) connection to pre-configured Wi-Fi stations (an infrastructure network) or directly to another Wi-Fi enabled device (an ad hoc network); establish an authenticated connection to Internet-based storage servers; and transmit air quality estimates and raw values from the sensor M continuously. In other embodiments, the wireless transceiver subsystem 20 could use other wireless communication protocols, in addition to or in lieu of the WiFi protocol, such as ZigBee (IEEE 802.15.4), Bluetooth, or wireless USB, for example.

More details about such an exemplary environmental sensor are provided in U.S. patent application Ser. No. 14/684,542, filed Apr. 13, 2015, entitled "Air Quality Sensor," which is incorporated herein by reference in its entirety.

Figure 2:
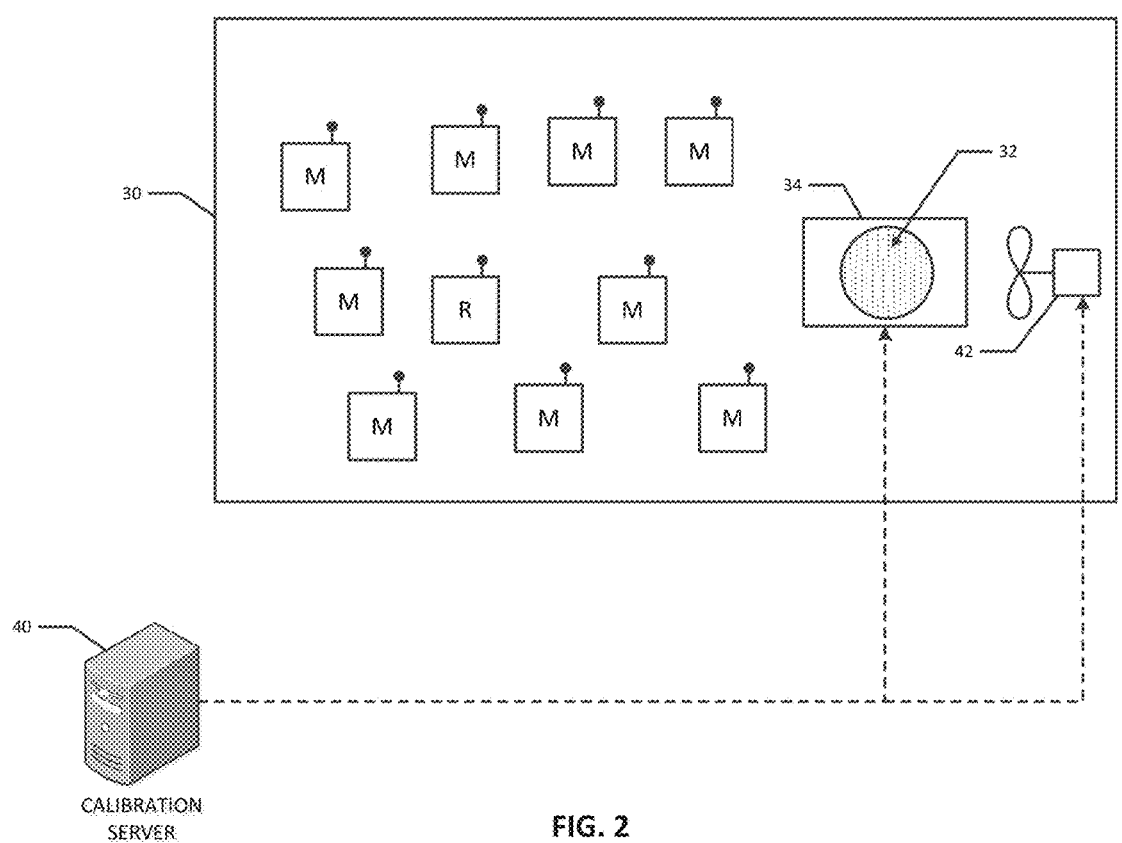
FIG. 2 is diagram of a calibration system for calibrating candidate air quality sensors according to various embodiments of the present invention.

Regardless of whether the environmental sensor uses the estimation algorithm described above or some other algorithm, the numerical parameters of the sensor's algorithm must be calibrated to yield useful readings. FIG. 2 is a block diagram of a system for batch calibrating a number of candidate environmental sensors M according to various embodiments of the present invention. Calibrating a number of candidate sensors in a group at once avoids the cost associated with calibrating each sensor separately, which should result in lower retail costs for the sensors. Additionally, calibrating multiple sensors simultaneously allows for identification of sensors with outlying behavior through statistical cross-correlation.

As shown in FIG. 2, the candidate sensors M to be calibrated can be placed within an enclosure 30, e.g., a calibration chamber, with one or more reference environmental sensor(s) R. The reference sensor R is preferably a high-performance, typically laser-based (as opposed to LED), calibrated particle-counting devices, such as a HHPC-6 and/or a HHPC-6+ particle counter. The calibration chamber 30 could be a room, or it could be a smaller, specialized calibration enclosure. A specialized calibration chamber provides the advantage that it reduces human exposure to the fine particles used in the calibration process, makes it easier to collect the particles afterward for reuse, and allows for better control of the enclosure environment (more homogenous particle concentration).

As shown in FIG. 2, the calibration system also includes a particle excitation system for dispersing particles throughout the volume of the calibration chamber 30. To that end, the excitation system may comprise an open container 32 of fine particles (e.g., $PM_{2.5}$ particles) that sits on top of a vibration system 34 such that when the vibration system 34 is operated, it vibrates the particle container 32 such that the fine particles in the container drift into the ambient air of the enclosure 30. The vibration system 34 may comprise, for example, a loudspeaker, such as a sub-woofer, or some other vibrator suitable for vibrating the particle container 32 so that the fine particles therein are dispersed throughout the volume of the calibration chamber 30. The amplitude and frequency of the vibrations of the vibration system 34 can be controlled by a calibration server 40, as described in more detail below, to thereby control the environmental state of the calibration chamber 30. In particular, changing the amplitude changes the number of particles dispersed into the calibration chamber 30 (higher amplitude, more particles), whereas varying the frequency varies the size of the particles emitted into the calibration chamber 30 (higher frequency, lower average particle size). The vibration system 34 can nominally operate at around 100 Hz or so, for example. The calibration system may also include a fan 42 for distributing the particles throughout the calibration chamber 30. The fan 42 can also be controlled by the calibration server 40 as described further below.

Each of the candidate sensors M and the reference sensor(s) R is in communication with the calibration server 40 via a wired or wireless communication link. For example, when a WiFi communication link is used, the sensors M may establish direct, ad hoc Wi-Fi communication links with the calibration server 40 or they may communicate through an infrastructure Wi-Fi network (e.g., communication to the network through one or more wireless access points (not shown)). The reference sensor R could also be in communication with the calibration server 40 via a Wi-Fi network just like the candidate sensors M. Other wireless protocols besides Wi-Fi could also be used, such a ZigBee, Bluetooth or wireless USB as described above. Additionally, any or all of the candidate or reference sensors can have a wired, two-way data connection to the calibration server 40. The calibration server 40 can also be in communication with the vibration system 34 and/or the fan 42 via wired and/or wireless communication links to provide a feedback loop for the particle excitation system. That is, for example, if the particle concentration from the sensors (particularly the reference sensor(s) R) is not at the desired level, the calibration server 40 can adjust the vibration system 34 (e.g., the amplitude of the vibrations or frequency) and/or the fan 42 until the particle concentration in the enclosure is at the desired level.

During the calibration process, the vibration system 34 is actuated such that particles from the container 32 are emitted into the volume of the calibration chamber 30. The fan 34 can optionally blow the particles around the calibration chamber 30. The sensors M, R continuously report their time-stamped environmental readings (e.g., particle concentration readings) to the calibration server 40. Each sensor M, R also has an ID or address that is reported to the calibration server 40 so that the server 40 can record each sensors' readings over time.

The calibration server 40 may be programmed to, among other things:

- Collect and record the time series environmental readings from the sensors M, R;
- Control the ambient in conditions in the calibration chamber 30 based on the environmental readings, particularly based on the high-performance reference sensor R, by controlling the vibration system 34 (e.g., controlling amplitude and/or frequency) and/or controlling the fan 42, to achieve known and measurable particle concentration levels over a dynamic range;
- Identify candidate sensors M" that are not acceptable;
- Compute the calibration values for the respective candidate sensors M' that are acceptable and transmit those values back the acceptable candidate sensors M'; and
- Archive the calibration values in a memory unit of the calibration server 40.

Figure 3:
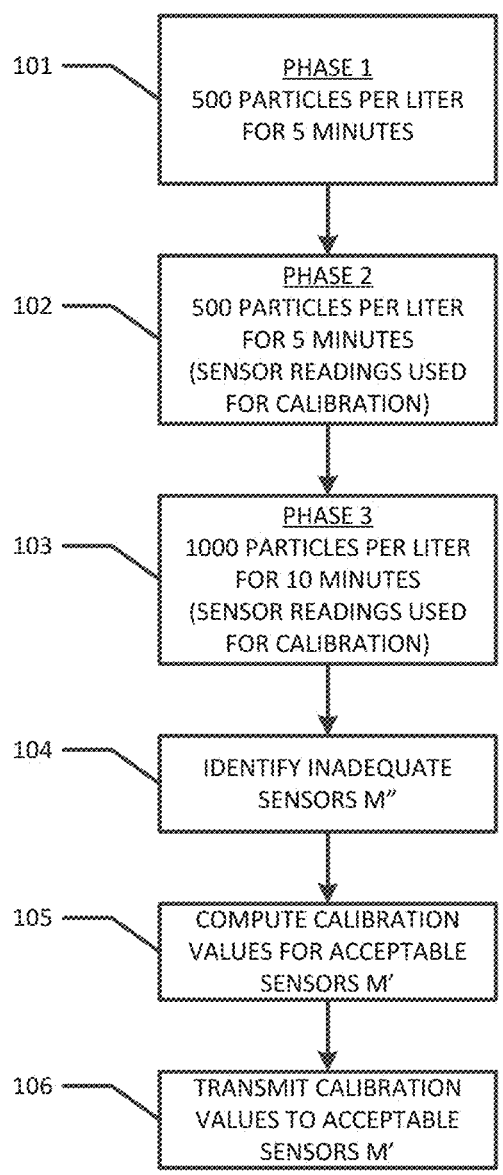
FIG. 3 is a flow chart of the calibration process implemented by the calibration system of FIG. 2 according to various embodiments of the present invention.

FIG. 3 is a flow chart of an exemplary calibration process according to various embodiments of the present invention. At step 101, in a first phase of the calibration process, the excitation system is powered on and the particle concentration level is adjusted to a target of, for example, 500 particles per liter. All sensors M, R are turned on such that they collect and continuously report to the calibration server 40 their respective environmental readings. The readings from the sensors M, R are preferably all of the same type for the various phases so that they can be compared. Phase 1 may last for a brief period of time, such as five minutes, to allow all sensors M, R to reach equilibrium (e.g., a homogenous environment). As such, the readings from Phase 1 are not used in the calibration process in various embodiments. Any sensor M that cannot establish a connection to the calibration server 40 for some reason during Phase 1 can optionally be removed physically from the calibration chamber 30 or just ignored for the remainder of the calibration process.

At step 102, in Phase 2, the particle concentration is maintained at the level of Phase 1 (e.g., 500 particles per liter) for a period of time (e.g., five minutes). The sensors M, R continue reporting their time-series environmental readings to the calibration server 40 during the time period of Phase 2.

At step 103 in Phase 3, the particle concentration can be increased, such as doubled (e.g., 1000 particles per liter) for a period of time. The duration of the time period for Phase 3 can be the same or different than the duration of the time period for Phase 2, but is preferably longer, such as twice as long (e.g., 10 minutes) to allow time for the particle concentration to ramp up to the heightened concentration level and the sensors reach equilibrium. Again, the sensors M, R continuously report their time-series environmental readings to the calibration server 40 during the time period of Phase 3. The average size of the particles can be the same for Phases 1 through 3. That is, for example, the same container 32 or containers with identical particle characteristics can be used for the each phase, such that the average size of the particles in the ambient air of the calibration chamber is roughly dictated by the average size of the particles in the container 32 (subject to possible variations in size due to changes in frequency of the vibration system 34). The average particle size can be, for example, two microns in diameter for each phase of the calibration process.

In this example, the resulting dataset contains 15 minutes of data from each sensor M, R (assuming Phase 2 is five minutes and Phase 3 is ten minutes). The sensors M, R may report their readings every second, for example, to the calibration server, for a total of 900 data points per sensor M, R in this example. At step 104, the server 40 can identify for removal (or to ignore) sensors M" whose readings excessively deviate from the norm. For example, for each pair of sensors, the server 40 can compute the $r^2$ correlation coefficient, which can be stored in a square matrix, such as shown below (assuming n candidate sensors M).

$$\begin{array}{c} \\ M1 \\ M2 \\ \vdots \\ Mn \end{array} \begin{array}{cccc} M1 & M2 & \ldots & Mn \\ \left[ \begin{array}{cccc} \text{-} & \text{-} \text{-} \text{-} \text{-} \text{-} \text{-} \text{-} \text{-} \text{-} \text{-} \text{-} \text{-} \text{-} \text{-} & \text{-} \\ & \text{-} \text{-} & & \\ & & \ddots & \\ & & & \text{-} \text{-} \end{array} \right] \end{array}$$

The server 40 then can compute the average $r^2$ correlation coefficient for each candidate sensor M (i.e., average the values in one row of the matrix, such as indicated by the dashed box above for sensor M1). Candidate sensors M" whose average $r^2$ correlation coefficient is below some threshold value (e.g., 80%) can be removed since their readings were not closely correlated to the other sensors in the enclosure, even though the conditions in the enclosure were roughly the same (homogenous) for every sensor.

Then, at step 105, the calibration server 40 optimizes the algorithm constants for each remaining sensor M' (the sensors not removed at step 104). The algorithm constants can be optimized for each sensor M', for example, by minimizing the absolute percentage error between the sensor M' and the reference sensor R. If multiple reference sensors are used (such as in one enclosure or if there are multiple simultaneous batch calibrations each with their own reference sensor), the reference sensor R that is spatially closest to the subject sensor M' can be used for the optimization. The server 40 could be pre-programmed with data about the spatially closest reference sensor R for each candidate sensor M in this situation, for example. Then, at step 106, the calibration server 40 can transmit the optimized algorithm values for each remaining sensor M' to that sensor. The sensors M' store their respective calibrated algorithm values in memory 16 such that the sensors M' use them in the field when measuring air quality. The server 40 can also store the calibration values for each sensor M'.

The time periods, particle concentrations and average particle sizes for the calibration phases can differ from the examples described above in other variations of the inventive calibration process. Also, the steps shown in FIG. 3 could be performed in different orders or some steps could be performed simultaneously, all within the scope of the present invention.

The calibration server 40 may comprise a central processing unit (CPU) that comprises one or more microprocessors. The server 40 may also comprise primary and second computer memory. Software for programming the server 40 to perform the functions described herein, including the calculations for classifying acceptable sensors and for determining their calibration values, can be stored in the computer memory and executed by the CPU. The primary memory can comprise RAM; the secondary computer memory can comprise magnetic, optical or semiconductor memory, such as HDDs, SSDs, optical disks, and/or magnetic tapes, for example. The calibration server 40 could be replaced by another similarly programmed computer devices (or a network of such devices), such as a workstation, personal computer, laptop, tablet computer, smartphone, etc.

In various embodiments, therefore, the present invention is directed to a system for calibrating environmental sensors. With reference to FIG. 1, the system comprises the calibration chamber 30 and the calibration server 40. The calibration chamber 30 comprises a plurality of environmental sensors, including one or more candidate environmental sensors M to be calibrated and at least one reference environmental sensor R. The calibration chamber 30 also comprises the particle excitation system for changing the environmental state of the calibration chamber.

The calibration server 40 is in communication (e.g., wired or wireless communication) with the plurality of environmental sensors M, R and the particle excitation system. The environmental sensors M, R comprise circuitry for reporting their respective environmental readings to the calibration server 40. The calibration server 40 is programmed to control the particle excitation system to expose the plurality of environmental sensors to known and measurable environmental states (e.g., different particle concentration levels) across a dynamic range based on the environmental readings reported at least one of the environmental sensors M, R. The calibration server 40 classifies each of the one or more candidate environmental sensors M into two or more classes based on the environmental readings reported from at least the candidate environmental sensors, where the two or more classes comprise an unacceptable class and an acceptable class. For each of the acceptable candidate environmental sensors M', the calibration server 40 determines calibration values and transmits those calibration values to the acceptable candidate environmental sensors M', which the acceptable sensors M' store in their on-board memory 16.

In various embodiments, the particle excitation system comprises a vibration system 34 and an open container 32 of particles on the vibrator. The particle excitation system can further comprise a fan 42. The calibration server 40 can control the amplitude and frequency of vibrations from the vibration system 34 to dynamically control the environmental state of the calibration chamber 30.

In addition, the environmental sensors in the calibration chamber can comprise optical particle sensors. Some or all of the candidate environmental sensor(s) M can comprise a LED light source, and the reference environmental sensor(s) R can comprise a laser light source. The environmental readings reported from the environmental sensors M, R to the calibration server 40 can comprise particle concentration readings, such as volume-based particle concentration readings (e.g., particles per cubic centimeter) or mass-based particle concentration readings (e.g., milli- or micrograms per cubic centimeter). The environmental sensors M, R can also report their respective environmental readings over time, such that the calibration server 40 receives time-series particle concentration readings.

In various embodiments, the calibration chamber 30 comprises two or more reference environmental sensors R, and the calibration values for each acceptable candidate environmental sensor M' are determined by the calibration server 40 based on the reference environmental sensor R that is spatially closest to the acceptable candidate environmental sensor M' in the calibration chamber 30. The calibration server 40 can be programmed to determine the calibration values by, for each of the acceptable candidate environmental sensors M', minimizing errors of the environmental readings by the acceptable candidate environmental sensor M' relative to the spatially-closest reference candidate sensor R over two or more environmental states (e.g., the Phase 2 and Phase 3 states). Also, where the calibration chamber 30 comprises a plurality of candidate environmental sensors M, the calibration server 40 can be programmed to classify the candidate environmental sensors M based on computed correlation coefficients for each candidate environmental sensor to the other candidate environmental sensors over two or more environmental states (e.g., the Phase 2 and Phase 3 states). To that end, the calibration server 40 can compute an average correlation coefficient (e.g., an average correlation coefficient) for each of the candidate environmental sensors M and classify as acceptable candidate environmental sensors M whose average correlation coefficient is above a threshold value.

In another general aspect, the present invention is directed to a method of calibrating one or more candidate environmental sensors. The method comprises placing a plurality of environmental sensors in a calibration chamber 30. The plurality of environmental sensors comprises one or more candidate environmental sensors M to be calibrated and at least one reference environmental sensor R. The method further comprises the step of controlling the environmental state of the calibration chamber 30 to expose the environmental sensors M, R to known and measurable environmental states across a dynamic range. The method further comprises, for each of the one or more candidate environmental sensors M, classifying, by a calibration server 40 that is in communication with the plurality of environmental sensors M, R, the candidate environmental sensors M into two or more classes based on environmental readings from at least the candidate environmental sensors, where the two or more classes comprise an unacceptable class and an acceptable class. The method further comprises, for each of the one or more candidate environmental sensors classified as acceptable, (i) determining, by the calibration server 40, calibration values and (ii) transmitting, by the calibration server 40, the calibration values to the candidate environmental sensors M'.

In another general aspect, the present invention is directed to a method of manufacturing a candidate environmental sensor M. The method comprises the step of placing the candidate environmental sensor M and at least one reference environmental sensor R in a calibration chamber 30. The method further comprises the step of controlling an environmental state of the calibration chamber 30 to expose the candidate environmental sensor M and the at least one reference environmental sensor R to known and measurable environmental states across a dynamic range. The method further comprises the step of determining, by a calibration server 40 that is in communication with the candidate environmental sensor M and the at least one reference sensor R, whether the candidate environmental sensor M is acceptable based on environmental readings from the candidate environmental sensor M. Upon a determination that the candidate environmental sensor M is acceptable, the method further comprises (i) determining, by the calibration server 40, calibration values for the candidate environmental sensor M, (ii) transmitting, by the calibration server 40, the calibration values to the candidate environmental sensor M, and (ii) storing, by the candidate calibration sensor M, the calibration values transmitted by the calibration server.

While various embodiments have been described herein, it should be apparent that various modifications, alterations, and adaptations to those embodiments may occur to persons skilled in the art with attainment of at least some of the advantages. The disclosed embodiments are therefore intended to include all such modifications, alterations, and adaptations without departing from the scope of the embodiments as set forth herein.

What is claimed is:

1. A system for calibrating fine airborne particle sensors, the system comprising:
   a calibration chamber that comprises:
      a plurality of fine airborne particle sensors comprising:
         one or more candidate fine airborne particle sensors to be calibrated; and
         at least one reference fine airborne particle sensor, wherein the at least one reference fine airborne particle sensor is pre-calibrated; and
      a particle excitation system configured to disperse fine airborne particles throughout the calibration chamber at controllable levels to thereby change a fine airborne particle concentration state of the calibration chamber; and
   a calibration server that is in communication with the plurality of fine airborne particle sensors and the particle excitation system,
   wherein:
      the plurality of fine airborne particle sensors comprise circuitry for reporting their respective fine airborne particle readings to the calibration server; and
      the calibration server is programmed to:
         control the particle excitation system to expose the plurality of fine airborne particle sensors to known and measured fine airborne particle concentration states across a dynamic range, wherein the fine airborne particle concentration states are measured by at least one of the plurality of fine airborne particle sensors;
         for each of the one or more candidate fine airborne particle sensors, classify the candidate fine airborne particle sensors into two or more classes based on the fine airborne particle readings from at least the one or more candidate fine airborne particle sensors, wherein the two or more classes comprise an unacceptable class and an acceptable class; and
         for each of the one or more candidate fine airborne particle sensors classified as acceptable:
            determine calibration values for the one or more acceptable candidate fine airborne particle sensors, wherein the calibration values are determined based on the fine airborne particle readings from the one or more acceptable fine airborne particle sensors and the at least one reference fine airborne particle sensor; and
            transmit the calibration values to the one or more acceptable candidate fine airborne particle sensors.

2. The system of claim 1, wherein the particle excitation system comprises:
   a vibration system; and
   an open container of particles on the vibration system.

3. The system of claim 2, wherein the particle excitation system further comprises a fan.

4. The system of claim 2, wherein the calibration server controls the vibration system to control the particle concentration state of the calibration chamber.

5. The system of claim 1, wherein the plurality of fine airborne particle sensors comprises optical particle sensors.

6. The system of claim 5, wherein the one or more candidate fine airborne particle sensors each comprise a LED light source.

7. The system of claim 6, wherein the at least one reference fine airborne particle sensor comprises a laser light source.

8. The system of claim 1, wherein the fine airborne particle readings comprise volume-based particle concentration readings.

9. The system of claim 1, wherein the fine airborne particle readings comprise mass-based particle concentration readings.

10. The system of claim 1, wherein the fine airborne particle readings comprise time-series particle concentration readings.

11. The system of claim 1, wherein the calibration server is in wireless communication with at least one of the plurality of fine airborne particle sensors.

12. The system of claim 11, wherein:
   the calibration chamber comprises two or more reference fine airborne particle sensors; and
   the calibration values for each acceptable candidate fine airborne particle sensor are determined by the calibration server based on the reference fine airborne particle sensor that is spatially closest to the acceptable candidate fine airborne particle sensor in the calibration chamber.

13. The system of claim 1, wherein:
   the calibration chamber comprises a plurality of candidate fine airborne particle sensors; and
   the calibration server is programmed to classify the plurality of candidate fine airborne particle sensors based on computed correlation coefficients for each candidate fine airborne particle sensor relative to the other candidate fine airborne particle sensors over two or more particle concentration states.

14. The system of claim 13, wherein the calibration server is programmed to:
   compute an average correlation coefficient for each of the plurality of candidate fine airborne particle sensors; and
   classify as acceptable candidate fine airborne particle sensors whose average correlation coefficient is above a threshold value.

15. The system of claim 13, wherein the calibration server is programmed to determine calibration values by, for each of the one or more acceptable candidate fine airborne particle sensors, minimizing errors of the fine airborne particle readings by the acceptable candidate fine airborne particle sensor relative to the one or more reference fine airborne particle sensors over two or more particle concentration states.

16. A method of calibrating one or more candidate fine airborne particle sensors, the method comprising:
   placing a plurality of fine airborne particle sensors in a calibration chamber, wherein:
      the plurality of fine airborne particle sensors comprises:
         one or more candidate fine airborne particle sensors to be calibrated; and at least one reference fine airborne particle sensor, wherein the at least one reference fine airborne particle sensors is pre-calibrated;

dispersing particles throughout the calibration chamber to expose the plurality of fine airborne particle sensors to known and measured fine airborne particle concentration states across a dynamic range, wherein the fine airborne article concentration states are measured by at least one of the plurality of fine airborne particle sensors;

for each of the one or more candidate fine airborne particle sensors, classifying, by a calibration server that is in communication with the plurality of fine airborne particle sensors, the candidate fine airborne particle sensors into two or more classes based on fine airborne particle readings from at least the one or more candidate fine airborne particle sensors, wherein the two or more classes comprise an unacceptable class and an acceptable class; and for each of the one or more candidate fine airborne particle sensors classified as acceptable:
  determining, by the calibration server, calibration values for the one or more acceptable candidate fine airborne particle sensors, wherein the calibration values are determined based on the fine airborne particle readings from the one or more acceptable fine airborne particle sensors and the at least one reference fine airborne particle sensor; and
  transmitting, by the calibration server, the calibration values to the one or more acceptable candidate fine airborne particle sensors.

17. A method of manufacturing a candidate fine airborne particle sensor, the method comprising:

placing the candidate fine airborne particle sensor and at least one reference fine airborne particle sensor in a calibration chamber, wherein the at least one reference fine airborne particle sensor is pre-calibrated;

dispersing particles throughout the calibration chamber to expose the candidate fine airborne particle sensor and the at least one reference fine airborne particle sensor to known and measured particle concentration states across a dynamic range, wherein the fine airborne article concentration states are measured by at least one of the candidate fine airborne particle sensor or the at least one reference fine airborne particle sensor;

determining, by a calibration server that is in communication with the candidate fine airborne particle sensor and the at least one reference sensor, whether the candidate fine airborne particle sensor is acceptable based on fine airborne particle readings from the candidate fine airborne particle sensor; and upon a determination that the candidate fine airborne particle sensor is acceptable:
  determining, by the calibration server, calibration values for the candidate fine airborne particle sensor, wherein the calibration values are determined based on the fine airborne particle readings from the candidate fine airborne particle sensor and the at least one reference fine airborne particle sensor;
  transmitting, by the calibration server, the calibration values to the candidate fine airborne particle sensor; and
  storing, by the candidate fine airborne particle sensor, the calibration values transmitted by the calibration server.

* * * * *